United States Patent [19]

Getman

[11] Patent Number: 4,578,514

[45] Date of Patent: Mar. 25, 1986

[54] SYNTHESIS OF SULFILIMINES

[75] Inventor: Daniel P. Getman, St. Louis, Mo.

[73] Assignee: Monsanto Company, St. Louis, Mo.

[21] Appl. No.: 667,180

[22] Filed: Nov. 1, 1984

[51] Int. Cl.$^4$ ............................................ C07C 145/02
[52] U.S. Cl. ..................................................... 564/102
[58] Field of Search ........................................ 564/102

[56] References Cited

U.S. PATENT DOCUMENTS 3,576,836  3/1971  Prichard .
4,070,391  1/1978  Licke .
4,172,095  10/1979  Steinman et al. .................... 564/102

OTHER PUBLICATIONS

Strandtmann et al., J. Org. Chem. 36, p. 1742 (1971).
Needlein, Arch. Pharm., vol. 299 pp. 64–66 (1966).
Sorenson, J. Org. Chem. vol. 24, pp. 978–980 (1959).
Ozaki, Chemical Reviews 72, p. 469 (1972).
Needlein, Angew, Chem. Inter. Ed. vol. 4 pp. 708–709 (1965).
Kirk–Othmer Encyclopedia of Chemical Technology, 2nd edition vol. 19, pp. 328–330.
B. A. Arbuzov et al., Izv. Alad. Nawk USSR, Ser Khim. No. 5, 1206 (1975) (translation).
C. King, J. Org. Chem., 25, 352 (1960).

Primary Examiner—Charles F. Warren
Assistant Examiner—R. A. Picard
Attorney, Agent, or Firm—Joseph D. Kennedy; James W. Williams

[57] ABSTRACT

Processes are disclosed for preparation of N-aryl-S,S-dihydrocarbylsulfilimines by reaction of phenylisocyanate compounds with hydrocarbyl sulfoxides. The sulfilimines can be rearranged to ortho-thioalkylene anilines and the reactions can be employed in a route for converting nitrobenzene compounds to ortho-thioalkylene anilines, which are useful intermediates for preparation of herbicidal compounds.

24 Claims, No Drawings

SYNTHESIS OF SULFILIMINES

This invention relates to processes for preparation of N-aryl-S,S-dihydrocarbylsulfilimines by reaction of phenylisocyanate compounds with dihydrocarbyl sulfoxides, and to processes using such reaction in a route for converting nitrobenzene compounds to ortho-thioalkylene anilines.

BACKGROUND OF THE INVENTION

Sulfilimine compounds are of interest as intermediates in procedures for producing various o-alkylacetanilide compounds having herbicidal properties. Sulfilimines have previously been produced by reacting an aniline compound with dimethylsulfide in the presence of a source of positive chlorine, e.g. N-chlorosuccinimide. The N-phenyl-S,S-dimethylsulfilimine is then rearranged to an o-methylthiomethyl aniline, and the latter compound or derivative thereof is subjected to a reductive cleavage reaction to obtain an o-methylaniline. An electrolytic reductive cleavage reaction and further description of reactions leading to compounds with herbicidal properties is set forth in a commonly assigned copending application of Richard D. Goodin et al., Ser. No. 530,135, filed Sept. 7, 1983, and issued Jan. 15, 1985 as Patent No. 4,497,755 the disclosure of which is incorporated herein by reference. In the described procedures for producing sulfilimines it is necessary to have a source of positive chlorine, and it would be desirable to have a process which did not use such an agent and accompanying costs or need for recovery and regeneration procedures.

Certain activated isocyanate compounds have been reported to react with dimethyl sulfoxide at room temperature. Thus Arbuzov et al, Izv. Akad. Nauk. SSSR Ser, Khim, No. 5, pp. 1206–1207 (1975) states that trifluoroacetylisocyanate, as a strong electrophile, reacts with dimethyl sulfoxide to give N-trifluoroacetyl-S,S-dimethylsulfilimine, and C. King, J. Org. Chem. Vol. 25, pp. 352–356 (1960), shows conversion of p-toluenesulfonyl isocyanate to N-p-toluenesulfonyl dimethylsulfilimine.

Various aromatic isocyanates are reported to be produced by carbonylation of aromatic nitro compounds, generally at elevated temperatures and pressures with noble metal catalysts. The referred-to reports have not utilized the preparations in conjunction with reactions of the product with dimethyl sulfoxide to obtain sulfilimines, or with special compounds of interest for obtaining particularly desired products in the present invention, such as with o-nitro-trifluoromethylbenzene. U.S. Pat. Nos. 4,070,391 and No. 3,576,836 are among those describing carbonylation procedures in which aromatic nitro compounds are contacted at elevated temperatures and pressures with carbon monoxide in the presence of a noble metal catalyst, such as a palladium halide or a rhodium oxide. Such procedures, as well as those illustrated in the present specification, can be used in preparing isocyanates for conversion to sulfilimines in accord with the present invention. For example subatmospheric, atmospheric or superatmospheric pressures can be used, but elevated pressures are generally advisable to obtain good reaction rates with pressures generally in the range of about 500 to 10,000 psi (3447.5 to 68,950 KPa) and more commonly about 1500 to 5000 psi (10,342 to 34,475 KPa). Temperatures from ambient to 400° C. can be used, depending on the catalyst, with some being conveniently used at about 100° to 225° C., while others are employed about 150° to 225° C. or higher.

Aniline compounds can be converted to phenylisocyanate compounds by reaction with phosgene, and this procedure can be utilized to obtain isocyanate compounds for further reaction herein. This can serve as an indirect route from nitrobenzenes to isocyanates herein, as nitrobenzenes are readily reduced, as by hydrogenation, to aniline compounds. Particular aniline compounds, e.g. ortho-trifluoromethylaniline, can be converted to phenyl isocyanate compounds under conditions generally known in the art for such conversion of other aniline compounds. For example, the aniline compound in solution in an inert solvent can be contacted with phosgene, possibly at low temperature to condense the phosgene, and then reacted further by moderate heating, to 100°–150° C. or so, with further addition of phosgene, or with use of pressure vessel to maintain some phosgene content in the solution.

SUMMARY OF THE INVENTION

The invention involves the reaction of N-phenyl (including substituted phenyl) isocyanates with sulfoxide compounds to produce phenyl sulfilimines or rearrangement products thereof. The reaction is acid promoted. The invention further concerns a process for preparing ortho-alkyl anilines from nitrobenzenes, by carbonylating the nitrobenzenes to phenylisocyanates, reacting the phenylisocyanates with sulfoxides to produce N-phenylsulfilimines, rearranging the sulfilimines to ortho-hydrocarbylthioalkyl anilines and desulfurizing to orthoalkylanilines The invention particularly involves a process providing intermediate compounds for the production of N(ethoxymethyl)2'-methyl-6'-trifluoromethyl-2-chloroacetanilide, a herbicidal compound particularly effective against such perennial weeds as quackgrass and nutsedge in various crops. Thus o-nitrobenzotrifluoride is carbonylated to o-trifluoromethylphenylisocyanate, the isocyanate is reacted under acid catalyzed conditions with dimethylsulfoxide to produce N-(2-trifluoromethyl)-phenyl-S-S-dimethylsulfilimine which is rearranged to orthomethylthiomethyl, ortho-trifluoromethyl aniline, which can be desulfurized to orthomethyl, orthotrifluoromethylaniline. The latter compound can be reacted with chloroacetylchloride to obtain 2'-methyl-6'-trifluoromethyl-2-chloroacetanilide, which is then reacted with chlorometyl ethyl ether to obtain the N(ethoxymethyl)2'-methyl-6'-trifluoro-methyl-2-chloroacetanilide. The sulfilimine product from the reaction of the isocyanate can generally be purified readily as the by-product is carbon dioxide. The invention further involves use of particularly suitable catalysts and solvents for the reaction of the phenyl isocyanate, and reactions with phenylisocyanates having various substituents leading to products having desirable properties. As an alternate in the process from nitrobenzenes, the nitrobenzenes can first be reduced to anilines and the latter can be reacted with phosgene to obtain phenyl isocyanates, which can then be further reacted as described. In the processes to produce sulfilimines, or in their rearrangement, there may be some concomitant production of aniline compounds, and the aniline compounds can be converted to isocyanates by reaction with phosgene, and recycled to the reaction with sulfoxide compounds.

DETAILED DESCRIPTION OF THE INVENTION

The reaction of the phenylisocyanate with a sulfoxide compound and subsequent rearrangement can be illustrated:

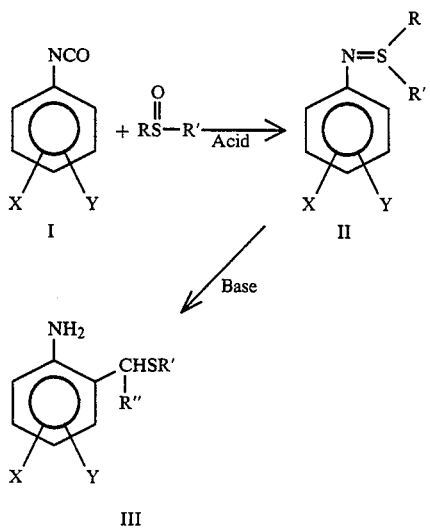

in which:
- X and Y are each selected from hydrogen or non-interfering substituents
- R and R' are each selected from hydrocarbyl groups
- R"CH is a hydrocarbyl group like R but with one less methylene group;

In the illustrated reaction, the isocyanate group is directly bonded to the benzene ring. It has been found that such isocyanates are amenable to reaction with sulfoxides in the presence of a suitable acid catalyst. The fact that the reaction utilizes a phenylisocyanate as a reactant is important in that the product can be rearranged to an orthoalkyl aniline, and such anilines are of great interest as precursor compounds for various herbicidal and similar compounds. The reaction occurs with phenyl isocyanates containing no additional substituents on the phenyl ring, and in general occurs without regard to the presence of such substituents. Various substituents can be used and may have some effect on the rate of the reaction and selectivity to, and stability of, the sulfilimine product, while not determining operability of the process. Thus the substituents used will generally be selected on the basis of known or projected effect on product properties, or comparative availability or ease of preparation of starting materials. Trifluoromethyl substituents are of special interest, particularly when in ortho position to the isocyanato group. Other groups which X and Y can represent include —CN, —NO₂, —Cl, —CH₃, —OCH₃, —CO₂ alkyl, as well as —H, and such groups can be in various positions, such as ortho, meta or para to the isocyanato group, e.g. p—CN, p—NO₂, p—Cl, m—CF₃, o—CH₃, o—OCH₃, p—CO₂ ethyl, etc. X and Y can be the same or different, and when both are hydrogen, the benzene ring is unsubstituted except for the isocyanato group. Many compounds of interest will have only one substituent in the benzene ring of the phenyl isocyanate, with X or Y being hydrogen, and the other being one of the above-described groups. However, two or more of the above or other groups can be present as substituents in the phenylisocyanates which are converted to corresponding sulfilimines in accord with the process described herein, X and Y can be various alkyl or alkoxy groups in addition to those illustrated, with lower alkyl or lower alkoxy generally being of most interest, for example, those with 1 to 6 carbon atoms. Also X and Y can be any of the halogens, although chlorine and to some extent fluorine are more commonly used as substituents in herbicidal compounds. X and Y can also be halo alkyl groups in general, especially halomethyl, e.g. mono-, di- or trichloromethyl, and mono-, di- and trifluoromethyl. The substituents can be used separately, or in various combinations, as for example, ortho-trifluoromethylphenyl isocyanate, ortho,para-di(trifluoromethyl)phenyl isocyanate, para-chloro, ortho-trifluoromethylphenyl isocyanate, orthochloro, para-nitrophenyl isocyanate, meta-trifluoromethylphenyl isocyanate, para-methylphenyl isocyanate, ortho, para-dichlorophenyl isocyanate. Any of the illustrated substitutents can be used as the single substituent, i.e. with the other substituent being hydrogen, and it is also possible to utilize phenylisocyanates with more than two substituents. However ordinarily there would not be much purpose in reacting phenylisocyanates with two ortho-substituents, as one of the usual objectives of the present process is to provide some of the steps in a method of introducing an ortho-substituent into a compound in producing aniline compounds with ortho substituents.

The illustrated reaction involves a sulfoxide compound, which is characterized by an SO group in which the sulfur is bonded to two different carbon atoms. In the illustrated reaction above, the R and R' groups are generally hydrocarbyl groups, such as alkyl groups of 1 to 10 carbon atoms, or a phenyl group. The sulfoxide compound reacts with the aryl isocyanate, producing the sulfilimine with the R and R' groups still bonded to sulfur. In the subsequent rearrangement, the R group becomes bonded to the ortho-position of the benzene ring, with the bonding occurring at the carbon to which the sulfur is attached. Upon desulfurization of this thioether, an ortho-substituted aniline is obtained. The reactions are of particular interest for obtaining ortho-methylanilines, and hence dimethyl sulfoxide is preferred as the sulfoxide reaction. Other sulfoxides in which one of R and R' is methyl can also lead to o-thiomethylanilines and o-methylanilines. Other sulfoxides lead to corresponding products, e.g. di-n-propyl sulfoxide will produce N-phenyl-S,S-di-n-propylsulfilimine which can be rearranged to 2'[n-propylthio-(1-n-propyl)]aniline which will desulfurize to ortho-n-propylaniline. In the rearrangements of sulfilimines to thioalkylene aniline compounds, one of the methylene carbons attached to sulfur becomes attached directly to the benzene, e.g. an N-aryl-S,S-di-2-propyl sulfilimine would become a 2'[2-propylthio(2-propyl)]aniline. Since dimethyl sulfoxide is conveniently available, it will generally be the reagent of choice, particularly when the object is to produce an ortho-methyl aniline compound. However, other dialkyl sulfoxides will be useful to provide other alkyl groups in products, and there may be advantage in using sulfoxides in which the two alkyl groups are the same, in order to avoid the possibility of mixtures of products.

In the reaction to produce sulfilimines, one of the ortho positions in the phenylisocyanate will generally be free of substituents, as the object of the reactions is frequently to introduce an ortho-alkyl substituent and to provide an ortho-alkyl aniline compound.

The process for preparing sulfilimines in accord with the present invention involves contacting a phenyl isocyanate with a sulfoxide in the presence of an effective strong acid catalyst. It is not necessary to have a solvent present, but there will generally be some separation of phases in the absence of solvent. Some of the isocyanate reactants are liquids, which contributes to intermixing of reactants. Also excess of the sulfoxide, particularly dimethyl sulfoxide, can serve as a solvent. Solvents can be usefully employed to bring the components into a single phase for reaction, and solvents which solubilize the reaction components are suitable, provided they do not unduly interfere with the desired reaction. Solvents which are relatively inert are preferred. Among solvents which can be used are acetic acid or other alkanoic acids, chloroform, acetonitrile, sulfuric acid, dimethyl sulfoxide, tetramethylene sulfoxide and N-methylpyrrolidinone. Other chlorinated hydrocarbon solvents can be employed, e.g. methylene chloride and dichloroethane. Alkanes, including alicyclic and cycloalkanes can be used, e.g. hexane and cyclohexane, but such solvents are generally less efficient as solvents for the reactants and products than some of the chlorinated solvents, acetonitrile, etc.

A strong acid is employed to cause the reaction to occur, as little or no reaction occurs in the absence of such agent. The acid should be one which causes the reaction to occur, but which does not unduly interfere by causing other reactions of the components. Sulfur containing acids, such as the various sulfonic acids and sulfuric acid are suitable, including ion exchange resins with sulfonic acid groups. Examples of acids which can be used are sulfuric acid, methanesulfonic acid, butanesulfonic acid, other alkane sulfonic acids, p-toluenesulfonic acid, and Amerlyst XN-1010 ion exchange resin, an ion exchange resin characterized by acidic groups, being a polystyrene with sulfonate groups (—SO$_3$H). Sulfurous acid, and other sulfur acids can also be used. It will generally be desirable to employ anhydrous, or virtually anhydrous, acids, as isocyanates react with water, and any water present may interfere with the desired reaction or, to some extent, use up the isocyanate reactant until all the water has reacted. Acetic acid is also capable of reacting with isocyanates, but can nevertheless be used as a solvent, particularly with provisions to have adequate sulfoxide and strong acid present for the isocyanate to react in the desired manner to produce sulfilimine. An acid is necessary to effect the desired sulfilimine preparation. It can readily be determined if an acid is effective for such purpose. In the absence of an acid, no appreciable reaction occurs even on heating to in excess of 100° C., as evidenced by lack of observable reaction and determination of unchanged reactant. In the presence of effective acid, there will be gas evolution upon bringing the reactants together, and there will be reaction between the isocyanate and sulfoxide and sulfilimine will be produced, as determinable by analysis.

In the presence of strong acid, the reaction of phenyl isocyanates and dihydrocarbyl sulfoxide occurs during contact without the application of heat. Since the reaction is exothermic, provision may be made for heat removal or controlling addition of reactants to avoid excessive exotherms. In laboratory procedures, slow or dropwise addition of one reactant, generally the isocyanate, to the reaction mixture is appropriate, but other procedures for cooling or heat transfer may be better suited to large-scale operation. With sulfuric acid as the strong acid agent, there is heat evolution upon mixing with the sulfoxide and solvent, which can be controlled by cooling or other suitable means. The strong acid agent does not become part of the sulfilimine product, but even so appears to react in stoichiometric fashion with the other reactants, possibly forming a salt or complex at some stage of the reaction. In order to have complete reaction, it is desirable to have the strong acid present in at least about equimolar amount to the reactants, and the acid may be employed in slight or considerable excess over equimolar amount. The phenyl isocyanate and sulfoxide react in an equimolar reaction, so will generally be employed in substantially equimolar quantities in order to have complete reaction. In order to promote complete reaction of one of the reactants, it may be desirable to employ the other reactant, e.g. the sulfoxide, in slight excess. When the isocyanate and sulfoxide reactants are used in unequal molar amounts, the amount of acid to use can be based on the reactant present in lesser amount. While the isocyanate and sulfoxide react in equimolar amounts, one or the other can be present in excess during the reaction as, for example, when gradually adding the isocyanate to a reaction mixture containing excess sulfoxide. There may be advantage with particular isocyanates in the use of excess of one of the reactants, in either batch or continuous reactions.

If a solvent is employed, the reactants can be used in widely varying concentrations in the solvent, but will generally be used in ranges to promote good reaction rates and solubility of reactants. Such concentrations will often be a range such that each of the isocyanate and sulfoxide reactants constitutes from about 5% to about 30% by weight of the solvent, based on the total of the reactant added during a batch reaction, and the amount of sulfoxide originally present may be, for example, about 10% or so by weight. The reaction to obtain sulfilimines will occur at ambient conditions, such as room temperature, or so, say around 24° to 30° C. However, if desired the temperature can be allowed to rise or the reaction mixture can be heated to temperatures up to 80° C. or higher, although in general the yields of sulfilimine will be better at lower temperatures, such as not over 40° C. or at room temperature or possibly even lower. As the reaction temperature is increased, there is more tendency toward decomposition reactions with production of aniline compounds corresponding to the starting isocyanate, thereby causing a decline in the production of the desired sulfilimine compound. In general there will not be much reason to exceed 100° C. or so, unless some particular reactants evidence poor reaction under usual conditions. If desired, low temperatures, such as temperatures well below ambient temperature can be used, with cooling means to effect same.

Since isocyanates react readily with water, it is desirable to exclude water from the solvents and other reaction system components. Many of the solvents are hygroscopic and readily pick up moisture from the air. The desired reaction can take place in the presence of moisture, but with some loss of yield. In order to guard against contamination by moisture, it is convenient to carry out the reaction under an inert atmosphere, as in an atmosphere of nitrogen or argon, but other moisture-free gases can also be used.

Following the reaction to produce the sulfilimine, the sulfilimine if sufficiently stable can be isolated. The reaction mixture is generally treated with base to neutralize the strong acid agent and convert any sulfilimine acid salt to the free sulfilimine. Aqueous base can conveniently be used for neutralization, as by slowly adding the reaction mixture to a large portion of aqueous sodium hydroxide. The sulfilimine can then be removed from the mixture by extraction with an organic solvent, e.g., methylene chloride or other solvent with capability of dissolving the sulfilimine. The organic solvent can then be removed by distillation to leave the isolated sulfilimine. While solvent extraction and distillation can be conveniently employed, other known methods of isolating organic compounds can be adapted to and used with particular sulfilimines.

Alternatively, the neutral sulfilimine obtained in the reaction can be rearranged to a thioalkylene aniline compound without isolation. After neutralization of the reaction mixture, for example with aqueous sodium hydroxide, the sulfilimine can be extracted into an organic solvent. If the original reaction solvent has sufficient solubilizing capability for the sulfilimine and the contemplated rearrangement catalyst, it can be employed to provide a solution for rearrangement. The rearrangement can conveniently be effected in an inert organic solvent which should have some solubilizing capability for both the sulfilimine and the rearrangement catalyst. A wide variety of organic solvents are available for selection, including, for example, methylene chloride, ethylene dichloride, cyclohexane, heptane and toluene. Ethylene dichloride is one of the preferred solvents. Succinimide is the preferred rearrangement catalyst, although other imide and other catalysts as disclosed herein can be used. Other preferred sulfilimine rearrangement catalysts include imidazole, glutarimide, phthalimide, 2-pyrrolidone, 2-imidazolidone and cyanuric acid. The arrangement catalyst can be used in varying amounts but generally about 0.5% to 25% (by mol.) based upon the sulfilimine is used, depending upon solubility of the particular catalyst in the organic solvent, and with succinimide as the catalyst, as little as about 2 mol percent is well suited for the desired catalysis. The rearrangement with succinimide and the other improved catalyts can be conveniently carried out over a wide range of temperatures. Typically, intermediate temperatures of about 35° to about 100° C. are preferred, particularly temperatures between about 60° to about 90° C. Alternatively, a solution of the sulfilimine can be heated for short periods under pressure at 120° to 180° C. to effect rearrangement. If desired, temperatures of about 110° to about 210° C. can be used to decrease the rearrangement times to a matter of minutes. The sulfilimine rearrangement can be conducted conveniently in refluxing solvent as an easy way to control reaction conditions. While succinimide and other preferred catalysts have certain advantages, it is also possible to conduct the rearrangement in the presence of dry base catalysts at elevated temperatures.

In the present invention the rearrangement of phenyl sulfilimines to o-thioalkyleneanilines is preferably carried out with succinimide or another member of a class of sulfilamine rearrangement catalysts selected from the groups consisting of:

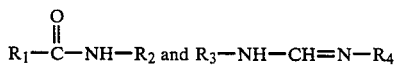

wherein $R_1$ can be a hydrogen, a lower alkyl or an —NH-alkyl and $R_2$ can be a hydrogen, a lower alkyl, an aryl or a

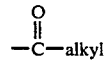

provided that $R_1$ and $R_2$ are not both hydrogens, or
$R_1$ and $R_2$ can be joined to form a cyclic compound having up to a 7-member ring, and $R_3$ and $R_4$ can be a hydrogen, or a lower alkyl; provided that $R_3$ and $R_4$ are not both hydrogens, or
$R_3$ and $R_4$ can be joined to form a cyclic compound having up to a 7-member ring.

The use of this class of rearrangement catalysts is described and claimed in commonly assigned application Ser. No. 529,914, filed Sept. 7, 1983, of Audrey Ku. While there are advantages to the described procedures and class of catalysts, the sulfilimines in the present invention can be rearranged in accord with any of the prior art procedures. Claus, Tetrahedron Letters, p. 3607 (1968), describes the preparation of aromatic sulfilimines from anilines and dimethylsulfoxide in the presence of $P_2O_5$ in a base such as triethylamine. Claus also discloses thermal rearrangement of these sulfilimines to ortho-(methylthiomethyl)anilines. See also, Gassman, Tetrahedron Letters, p. 497 (1972) and Johnson, Tetrahedron Letters, P. 501 (1972). Gassman discloses the use of N-t-butyl anilines to generate N-t-butyl-N-chloro anilines and subsequently sulfilimine salts with dimethyl sulfide which, upon treatment with a base under anhydrous conditions, were converted to ortho-(methylthiomethyl)anilines.

Such prior procedures in general involve anhydrous conditions, high temperatures, and the presence of alcohols and dry basic catalyst such as amines, for example triethylamine. In the present sulfilimine rearrangements, the rearrangement can be carried out with any sulfilimine rearrangement catalyst and the procedure may consist of heating the sulfilimine under basic conditions. Succinimide and other members of the class of rearrangement catalysts set forth above are considered bases, as they exhibit basic properties, but such compounds also exhibit acidic properties and may be particularly efficacious because of exhibiting both basic and acid properties.

The sulfilimines are often of interest as precursors to o-thioalkylene aniline compounds, and one of the objectives of the present invention is to prepare and utilize sulfilimines to prepare o-thioalkylene aniline compounds. As stated above, some sulfilimine compounds are relatively unstable, and in such instances it is convenient to rearrange such compounds prior to isolation. With sulfilimines which are stable, it will also often be convenient to rearrange such compounds prior to isolation. Following base treatment of the sulfilimine containing reaction mixture, the sulfilimine can be extracted into an organic solvent and rearranged. Alternatively, an isolated sulfilimine can be dissolved in an organic solvent and rearranged as described herein.

Aromatic sulfilimines with electron-withdrawing groups in ortho or para positions to the nitrogen atom tend to be relatively stable and susceptible to isolation. Thus trifluoromethyl, cyano, nitro and carbalkoxy substituents tend to stabilize the sulfilimines, However, sulfilimines with methyl, chloro, methoxy or no substituents tend to be unstable; while these compounds can be identified in solution and converted to methylthiomethyl aniline compounds, they are not readily suceptible to isolation, except in salt or other derivative forms.

As stated, sulfilimines with strongly electron-withdrawing groups will tend to be fairly stable, and this applies to those with groups having $\sigma_p^o$ values of at least 0.4, with the $\sigma_p^o$ value being that from the Hammett equation.

The Hammet equation is:

$$\log \frac{k}{k_o} = \sigma \rho$$

and for $XC_6H_4$:

$k_o$ is the rate constant for X=H
k is the constant for the group X
$\rho$ is the constant for a given reaction under given conditions
$\sigma$ is a constant characteristic of X Hammet $\sigma$ values are available for various group substituted at the p or m positions of phenyl rings. A positive value of $\sigma$ indicates an electron withdrawing group, and such groups help reactions in which $\sigma$ is positive. The $\sigma_p^o$ value contemplates reactions at site effectively insulated from $\pi$ electrons of the benzene rings. The Hammet equation and sigma values are discussed in "Advanced Organic Chemistry", Jerry March, 2nd Ed., McGraw-Hill, New York, N.Y., (1977), at pages 251–259, and $\sigma_p^o$ values are given in a table on page 256 which includes:

| Group | $\sigma_p^o$ |
|---|---|
| $CF_3$ | 0.54 |
| CN | 0.66 |
| $NO_2$ | 0.83 |
| $CH_3CO$ | 0.47 |
| $CO_2R$ | 0.46 |

Sulfilimines are useful for conversion to o-methylthiomethyl anilines regardless of stability, buty yields in the rearrangement reaction are generally better for the more stable sulfilimines. The unstable sulfilimines are more apt to undergo loss of the sulfur moiety to produce the aniline compound corresponding to the starting isocyanate, in some cases the product may include up to 30% or more of such aniline along with the desired o-methylthiomethylaniline compound. If desired, the concomitant aniline product can be reacted with phosgene or by other means to convert it to the corresponding isocyanate, and recycled to the sulfilimine preparation reaction.

Herbicidal compounds with the trifluoromethyl group in ortho position to an aromatic amino group are of particular interest, such as N-(ethoxymethyl)-2'-methyl-6'-trifluoromethyl-2-chloroacetanilide, and therefore the present process is of particular interest for converting o-trifluoromethylphenyl isocyanates to sulfilimines en route to production of 2-methyl-6-trifluoromethyl aniline, with the sulfilimine preparation being illustrated:

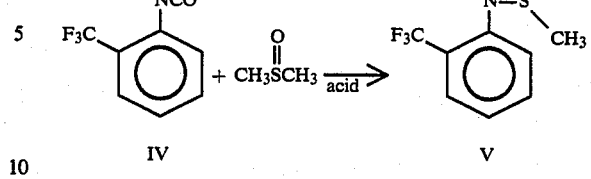

The sulfilimine compound V is relatively stable, so it can be isolated as such, or rearranged to 2-methylthiomethyl-6-trifluoromethylaniline before isolation, and the latter compound can be reductively cleaved to 2-methyl-6-trifluoromethylaniline.

The present invention is illustrated by the following examples but is not thereby limited. Some of the examples are included as comparison or control procedures.

EXAMPLE 1

Preparation of α, α, α-Trifluoro-o-tolyl Isocyanate by carbonylation of (α,α,α-Trifluoromethylnitrobenzene A solution of 0.67 (0.0037 moles) palladium dichloride, 0.60 g (0.0076 moles) pyridine, 7.23 g (0.0039 moles) of (α, α,α-trifluoromethyl)nitrobenzene and 0.9826 of tridecane as an internal standard in 75 ml of dry chlorobenzene was placed in a 300 ml Hastelloy C autoclave. After flushing with argon and carbon monoxide, the clave was charged with 2000 psi (13,790 KPa) of carbon monoxide and heated to 200° C. At 200° C., the pressure was increased to 3000 psi (20,684 KPa) and maintained at that temperature and pressure for four hours. A sample was withdrawn and analyzed by gas chromatography. This analysis showed that the solution contained 0.940 g (87% conversion) of (α,α,α-trifluoro-o-methyl)nitrobenzene and 5.85 g (95% selectively) of α,α,α-trifluoro-o-tolyl isocyanate.

EXAMPLE 2

Preparation of p-Chlor-(α,α,α-Trifluoro-o-tolyl) Isocyanate

A solution of 0.67 g (0.0039 moles) of palladium dichloride, 0.60 g (0.0076 moles) pyridine, 8.59 g (0.038 moles) of p-chloro-α,α,α-trifluoromethyl-nitrobenzene and 1.0040 g of tetradecane as an internal standard in 75 ml of dry chlorobenzene was placed in a 300 ml Hastelloy C autoclave. After flushing with argon and carbon monoxide, the clave was charged with 2000 psi (13,790 KPa) of carbon monoxide and heated to 200° C. At 200° C., the pressure was increased to 3000 psi (20,684 KPa) carbon monoxide and maintained at this temperature and pressure for four hours. A sample was withdrawn and analyzed by gas chromatography. This analysis showed that the solution contained 0.42 g (95% conversion) of p-chloro-α,α,α-trifluoromethylnitrobenzene and 7.46 (93% selectivity) of p-chloro-α,α,α-trifluoro-o-tolyl isocyanate.

EXAMPLE 3

Preparation of o-methoxyphenyl isocyanate

Into a 2 liter three-necked flask equipped with a dry ice condenser and an overhead stirrer, was condensed 100 ml of phosgene. At −5° C., was added a solution of 25 g (0.2032 moles) of o-anisidine in 350 ml of chlorobenzene and a heavy white precipitate was observed. The mixture was then heated at 125° C. for three and a half hours while passing phosgene slowly through the solution for the first hour and a half, and then nitrogen for the last two hours. The solution was then distilled to afford 27.0 g (89%) of o-methoxyphenyl isocyanate, bp 74°–76° C. at 3 mm Hg. 'H NMR ($\delta$,CDCL$_3$) 6.7–7.1 (multiplet, 4H) and 3.80 (s, 3H).

EXAMPLE 4

Control; Unreactivity of $\alpha,\alpha,\alpha$-Trifluoro-o-tolyl Isocyanate Towards Dimethyl Sulfoxide in the Absense of an Acid Catalyst A solution of 2.0274 g (0.013 moles) of dry dimethyl sulfoxide, 2.2369 g (0.012 moles of $\alpha,\alpha,\alpha$-trifluoro-o-tolyl isocyanate and 0.7709 g of dodecane as in internal standard in 10 ml of dry chloroform was refluxed for three hours under a nitrogen atmosphere. A sample was withdrawn and analyzed by gas chromatography. In this manner the solution was found to contain 2.23 g of $\alpha,\alpha,\alpha$-trifluoro-o-tolyl isocyanate indicating that no reaction had occurred.

EXAMPLE 5

Control; Unreactivity of $\alpha,\alpha,\alpha$-trifluoro-o-tolyl Isocyanate Towards Dimethyl Sulfoxide in the Absence of an Acid Catalyst A solution of 1.1538 g (0.015 moles) dry dimethyl sulfoxide, 2.3155 g (0.012 moles) $\alpha,\alpha,\alpha$-trifluoro-o-tolyl isocyanate and 0.7812 g of dodecane as an internal standard in 10 ml of dry toluene was refluxed under an argon atmosphere for four hours. A samples was withdrawn and analyzed by gas chromatography. In this manner the solution was found to contain 2.31 g of $\alpha,\alpha,\alpha$-trifluoro-o-tolyl isocyanate indicating that no reaction had occured.

EXAMPLE 6

Preparation of N-$\alpha,\alpha,\alpha$-trifluoro-o-tolyl)-s,s-dimethysulfilimine Using Sulfuric Acid in Acetic Acid To a solution of 1.13 g (0.014 moles) of dry dimethyl sulfoxide in 10 ml of dry acetic acid at 0° C. and under a nitrogen atmosphere, was slowly added 0.60 ml (1.35 g, 0.014 moles) of 100% sulfuric acid. The temperature rose to 15° C. The ice bath was removed and 2.2366 g (0.0120 moles) of $\alpha,\alpha,\alpha$-trifluoro-o-tolyl isocyanate was added dropwise. An immediate evolution of gas began which subsided after approximately fifteen minutes. After stirring at room temperature for two hours, the entire solution was poured into 150 ml of ice-cold 10% aqueous sodium hydroxide solution. After extraction with methylene chloride, the organic phase was dried over anhydrous sodium carbonate, filtered and the solvent was removed under reduced pressure to afford 2.6249 g of a white solid which was assayed by high pressure liquid chromatography (HPLC) to be 92.2%, by weight, of the desired sulfilimine. This corresponded to a yield of 2.4191 g (91.2%) of the sulfilimine. Other stable isolable N-aryl-S,S-dimethylsulfilimines were prepared and analyzed in a similar manner. The results can be found in Table I.

EXAMPLE 7

Preparation of N-($\alpha,\alpha,\alpha$-trifluoro-o-tolyl)-S,S-dimethylsulfilimine Using Sulfuric Acid in Acetonitrile To a solution of 1.12 g (0.014 moles) of dry dimethyl sulfoxide in 10 ml of dry acetonitrile at 0° C. and under a nitrogen atmosphere, was slowly added 0.60 ml (1.34 g, 0.014 moles) of 100% sulfuric acid. The temperature rose to approximately 15° C. The ice bath was removed and 2.2435 g (0.012 moles) of $\alpha,\alpha,\alpha$-trifluoro-o-tolyl isocyanate was added dropwise. An immediate evolution of gas began which subsided after approximately fifteen mintues. After stirring at room temperature for two hours the standard workup (see Example 6) afforded 2.6150 g of a white solid which was assayed by HPLC to be 94.0%, by weight, sulfilimine. This corresponds to a yield of 2.4591 g (92.7%) of the desired sulfilimine. The results are included in Table I.

EXAMPLE 8

Preparation of N-(p-chloro-$\alpha,\alpha,\alpha$-trifluoro-o-tolyl)S,S-dimethylsulfilimine Using Butanesulfonic Acid in Chloroform To a solution of 1.15 g (0.0147 moles) of dry dimethyl sulfoxide in 10 ml of dry chloroform at 15° C., was added 1.76 g (0.013 moles) of dry n-butanesulfonic acid. After the addition, 2.3125 g (0.0104 moles) of p-chloro-$\alpha,\alpha,\alpha$-trifluoro-o-tolyl isocyanate was added and the resulting mixture was stirred at room temperature for thirty minutes and then refluxed for three hours. The standard workup (see Example 6) afforded 2.6000 g of a white solid which was assayed by HPLC to be 92.9% by weight, sulfilimine. This corresponds to a yield of 2.4154 (90.4%) of the desired sulfilimine. The results are included in Table I.

TABLE I

Preparation of N—Aryl-S,S—dimethylsulfilimines

| Substrate | | Acid Catalyst | Solvent | Reaction Temperature | Yield of Sulfilimine |
|---|---|---|---|---|---|
| X | Y | | | | |
| o-CF$_3$ | H | H$_2$SO$_4$ | HOAc | 50° C. | 83.7% |
| o-CF$_3$ | H | H$_2$SO$_4$ | HOAc | 24° C. | 91.2% |
| o-CF$_3$ | H | H$_2$SO$_4$ | CH$_3$CN | 24° C. | 92.7% |
| o-CF$_3$ | H | H$_2$SO$_4$ | DMSO | 24° C. | 90.7% |
| o-CF$_3$ | H | n-BuSO$_3$H | CHCl$_3$ | 24° C. | 85.3% |
| o-CF$_3$ | H | n-BuSO$_3$H | CHCl$_3$ | 64° C. | 93.3% |
| o-CF$_3$ | p-Cl | H$_2$SO$_4$ | HoAc | 50° C. | 87.1% |
| o-CF$_3$ | p-Cl | n-BuSO$_3$H | CHCl$_3$ | 64° C. | 90.4% |
| p-CN | H | H$_2$SO$_4$ | HOAc | 50° C. | 63.6% |
| p-CN | H | n-BuSO$_3$H | CHCl$_3$ | 64° C. | 83.5% |
| p-NO$_2$ | H | H$_2$SO$_4$ | HOAc | 50° C. | 72.4% |
| p-NO$_2$ | H | n-BuSO$_3$H | CHCl$_3$ | 64° C. | 84.2% |
| p-CO$_2$Et | H | H$_2$SO$_4$ | HOAc | 50° C. | 89.0% |
| p-CO$_2$Et | H | n-BuSO$_3$H | CHCl$_3$ | 64° C. | 93.8% |

In Table I and elsewhere in this application n-Bu stands for n-butyl, HOAc for acetic acid, and DMSO for dimethyl sulfoxide.

EXAMPLE 9

Preparation of 2-(methylthiomethyl)aniline Using Sulfuric Acid in Acetic Acid

To a solution of 7.60 g (0.0974 moles) of dry dimethyl sulfoxide in 70 ml of dry acetic acid at 0° C. and under a nitrogen atmosphere, was slowly added 9.76 g (0.0959 moles) of 100% sulfuric acid. The temperature rose to 15° C. The ice bath was removed and 9.9843 g (0.0838 moles) of phenyl isocyanate was added dropwise. An immediate evolution of gas began, which subsided after approximately fifteen minutes. After thirty minutes at room temperature, the reaction mixture was warmed to 50° C. for an additional hour. The entire solution was then poured into 100 ml of 10% aqueous sodium hydroxide solution and this was extracted with methylene chloride. The organic layer was dried over anhydrous sodium carbonate and filtered. Due to the instability of this sulfilimine, 0.33 g of succnimide was added and the solution was then concentrated to 150 ml and refluxed for sixteen hours. The solution was then washed with 10% aqueous sodium hydroxide, dried over anhydrous magnesium sulfate and filtered. To this was added dodecane as an internal standard and the solution was analyzed by gas chromatography. In this manner, there was obtained 1.751 g (22.4%) of aniline and 7.166 g (55.8%) of 2-methylthiomethylaniline. Other examples of the preparation and rearrangement of unstable N-aryl-S,S-dimethylsulfilimines were performed and these results can be found in Table II.

EXAMPLE 10

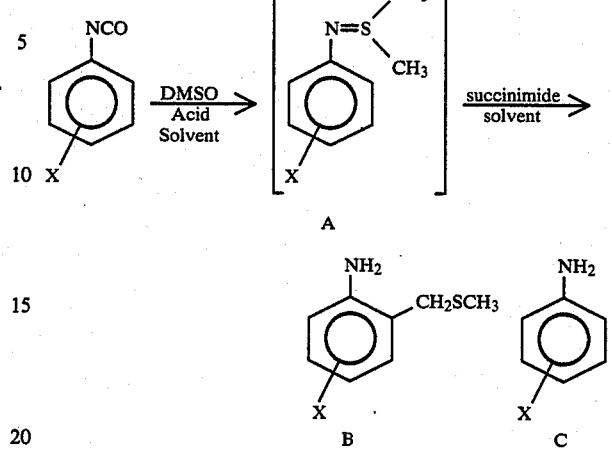

Preparation of 2-methoxy-6-(methylthiomethyl)aniline Using n-Butanesulfonic Acid in Chloroform To a solution of 1.429 g (0.018 moles) of dry dimethyl sulfoxide and 2.27 g (0.015 moles) of dry n-butanesulfonic acid in 13 ml of dry chloroform, was added 2.2110 g (0.0148 moles) of o-methoxyphenyl isocyanate. After thirty minutes at room temperature, the reaction mixture was refluxed for three and a half hours. After cooling to room temperature, the reaction mixture was poured into 180 ml of ice-cold 10% aqueous sodium hydroxide solution. After extracting with methylene chloride, the organic layer was dried over anhydrous sodium carbonate, filtered and 0.10 g of succinimide was added. The resulting solution was concentrated to 100 ml and then refluxed for twenty hours. This solution was cooled, extracted with 10% aqueous sodium hydroxide solution and the organic layer dried over anhydrous magnesium sulfate and filtered. At this point, tridecane was added as an internal standard and the solution was analyzed by gas chromatography. In this manner, there was obtained 0.338 g (22.4%) of o-methoxyaniline and 1.8319 g (67.6%) of 2-methoxy-6-(methylthiomethyl)aniline. The results are included in Table II.

In Table II, results are included for the following reaction.

TABLE II

Preparation of 2-(methylthiomethyl)aniline

| Substrate X | Preparation of Sulfilimine | | | Rearrangement of Sulfilimine | | Yield | |
|---|---|---|---|---|---|---|---|
| | Acid Catalyst | Solvent | Reaction Temp. | Solvent for Rearrang. | Temp. for Rearrang. | B | C |
| H | $H_2SO_4$ | HOAc | 50° C. | $CH_2Cl_2$ | 40° C. | 55.87 | 22.47 |
| p-Cl | $H_2SO_4$ | HOAc | 50° C. | $CH_2Cl_2$ | 40° C. | 73.9% | 1.6% |
| m-$CF_3$ | $H_2SO_4$ | HOAc | 50° C. | toluene | 110° C. | 77.3% | 6.6% |
| δ-$CH_3$ | $H_2SO_4$ | HOAc | 50° C. | $CH_2Cl_2$ | 40° C. | 52.2% | 22.0% |
| o-$CH_3$ | n-$BuSO_3H$ | $CHCl_3$ | 64° C. | $CH_2Cl_2$ | 40° C. | 76.8% | 13.77 |
| o-$CH_3$ | $H_2SO_4$ | $CH_3CN$ | 24° C. | $CH_2Cl_2$ | 40° C. | 40.3% | 35.6% |
| o-$OCH_3$ | $H_2SO_4$ | HOAc | 50° C. | $CH_2Cl_2$ | 40° C. | 40.3% | 35.6% |
| o-$OCH_3$ | n-$BuSO_3H$ | $CHCl_3$ | 64° C. | $CH_2Cl_2$ | 40° C. | 67.6% | 18.6% |

In Table III results are reported for various acids utilized in the reaction of 2-trifluoromethylphenyl isocyanate with dimethyl sulfoxide to obtain N-(2-trifluoromethylphenyl)-S,S-dimethyl sulfilimine.

TABLE III

Acid Catalysts for the Preparation of N—(α,α,α-Trifluoro-o-Tolyl)-S,S—dimethylsulfilimine

| Acid Catalyst | Solvent | Reaction Temperature | Yield Sulfilamine |
|---|---|---|---|
| $H_2SO_4$ | $CH_3CN$ | 24° C. | 92.7% |
| n-$BuSO_3H$ | $CHCl_3$ | 64° C. | 93.3% |
| p-tolyl $SO_3H$ | $CHCl_3$ | 64° C. | 71.1% |
| Amberlyst ® ion exchange resin | $CHCl_3$ | 40° C. | 47.0% |

In Table IV results are reported for reactions of 2-trifluoromethylphenylisocyanate with different sulfoxides to prepare sulfilimines, with sulfuric acid in acetonitrile.

TABLE IV

Reaction of Sulfoxides with α,α,α-Trifluoro-o-tolyl Isocyanate Preparation of Sulfilimines

| Sulfoxides $R_1S(O)R_2$ | | Acid Catalyst | Solvent | Reaction Temperature | Yield of Sulfilimines |
|---|---|---|---|---|---|
| $R_1$ | $R_2$ | | | | |
| $CH_3$ | $CH_3$ | $H_2SO_4$ | $CH_3CN$ | 24° C. | 92.7% |
| $CH_3$ | Ph | $H_2SO_4$ | $CH_3CN$ | 24° C. | 81.5% |
| n-Pr | n-Pr | $H_2SO_4$ | $CH_3CN$ | 24° C. | 57.8% |

In Table IV, n-Pr stands for n-propyl.

Reactions of 2-trifluoromethylphenyl isocyanate with dimethyl sulfoxide to obtain N-(2-trifluoromethylphenyl)-S-S,-dimethylsulfilimine were carried out, with results as reported in Table V.

TABLE V

Solvents for the Preparation of N—(α,α,α-Trifluoro-o-tolyl)-S,S—dimethylsulfilimine

| Acid Catalyst | Solvent | Reaction Temperature | Yield of Sulfilimine |
|---|---|---|---|
| H₂SO₄ | HOAc | 50° C. | 83.7% |
| H₂SO₄ | HOAc | 24° C. | 91.2% |
| H₂SO₄ | CH₃CN | 50° C. | 64.0% |
| H₂SO₄ | CH₃CN | 24° C. | 92.7% |
| H₂SO₄ | DMSO | 24° C. | 90.7% |
| H₂SO₄ | Tetramethylene sulfoxide | 50° C. | 33.2% |
| H₂SO₄ | N—methyl-pyrrolidinone | 50° C. | 46.1% |

EXAMPLE 11

Rearrangement of N-(2-trifluoromethylphenyl)-S,S-dimethyl sulfilimine

A sample of N-(2-trifluoromethylphenyl)-S,S-dimethylsulfilimine was heated at reflux in cyclohexane, with NMR spectroscopy evidencing no significant production of 2-methyl-6-trifluoromethylaniline. A 0.5 mol percent of succinimide was added to the refluxing mixture and reflux was continued for three hours. Rearrangement was complete as indicated by Fluorine NMR spectroscopy. A similar procedure was carried out with 22.1 grams of the sulfilimine and 0.1 of succinimide in 60 ml of ethylene dichloride. The reaction mixture was heated at reflux for 2 hours. A sample was withdrawn for NMR analysis and showed complete rearrangement of the sulfilimine to 2-methyl-6-methylthiomethylaniline. Gas chromatographic analysis indicated 91% of the stated aniline compound and 4% of ortho-aminobenzotrifluoride, i.e. ortho-trifluoromethylaniline obtained by hydrolysis of the sulfilimine during the rearrangement.

I claim:

1. The process of preparing N-phenyl sulfilimines which comprises reacting a phenyl isocyanate with a dihydrocarbyl sulfoxide in the presence of strong acid effective to cause reaction of isocyanate with sulfoxide, and producing such sulfilimines.

2. The process of claim 1 in which the sulfilimine is rearranged to produce the corresponding ortho-hydrocarbylthioalkyl aniline.

3. The process of claim 1 as represented by:

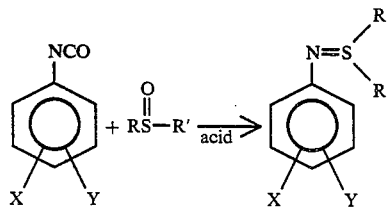

in which
X and Y are each selected from hydrogen or non-interfering substituents;
R and R' are each selected from hydrocarbyl groups.

4. The process as in claim 3 in which the resulting sulfilimine is rearranged to:

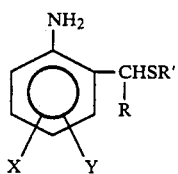

in which
X and Y and R' have the same meanings as in claim 3, and
R"CH is a hydrocarbyl group like R but with one less-methylene group.

5. The process of claim 3 in which X and Y are selected from trifluoromethyl, —CN, —NO₂, —CO₂, alkyl, —CH₃, —OCH₃ and —Cl.

6. The process of claim 3 in which 2-trifluoromethylphenyl isocyanate is reacted with dimethyl sulfoxide to produce N-(2-trifluoromethylphenyl)-S,S,-dimethylsulfilimine.

7. The process of claim 6 in which the sulfilimine is rearranged to form 2-(methylthiomethyl)-6-trifluoromethyl aniline.

8. The process of claim 4 in which 2-methoxyphenyl isocyanate is reacted with dimethyl sulfoxide and the resulting sulfilimine is rearranged to form 2-methoxy6-(methylthiomethyl)aniline.

9. The process of claim 3 in which X and Y are selected from trifluoromethyl, cyano, nitro and carbalkoxy at ortho and para positions.

10. The process of claim 1 in which a phenyl isocyanate and a dialkyl sulfoxide are brought into contact in a solvent with strong acid being supplied in amount at least about equimolar with the isocyanate reacted.

11. The process of claim 10 in which the reaction is permitted to occur at moderate temperatures up to about 80° C.

12. The process of claim 10 in which temperatures generally do not exceed 40° C.

13. The process of claim 10 in which the strong acid is selected from sulfuric acid and hydrocarbyl sulfonic acids.

14. The process of claim 10 in which a solvent present is selected from acetic acid, halogenated hydrocarbons, acetonitrile and dimethyl sulfoxide.

15. The process of claim 14 in which a strong acid is present selected from sulfuric acid and hydrocarbyl sulfonic acids.

16. The process of claim 15 in which 2-trifluoromethylphenyl isocyanate is reacted with dimethylsulfoxide to produce N-(2-trifluoromethylphenyl)-S,S-dimethylsulfilimine.

17. The process of claim 11 in which the isocyanate is added to an organic solvent containing the sulfoxide and strong acid.

18. The process of preparing ortho-alkylanilines which comprises directly or indirectly carbonylating a nitrobenzene to obtain a phenylisocyanate, reacting the phenylisocyanate with dialkyl sulfoxide under acidic conditions to obtain an N-phenyl-S,S-dimethylsulfilimine and rearranging same to a 2-alkylthioalkyl aniline, and reductively desulfurizing to obtain an ortho-alkylaniline.

19. The process of claim 18 in which the alkylthioalkyl moiety is converted to a sulfoxide, sulfone or sulfonium salt group before desulfurizing.

20. The process of claim 2 in which the product from the rearrangement includes an aniline compound corresponding to the 2-alkylthioalkyl aniline product except for absence of the 2-alkylthioalkyl substituent, and the process comprises converting such aniline to the corresponding phenyl isocyanate and recycling such phenyl isocyanate for reaction with the dialkyl sulfoxide.

21. The process of claim 20 in which the aniline is converted to the corresponding isocyanate by reaction with phosgene.

22. The process of claim 18 in which 2-trifluoromethylnitrobenzene is carbonylated to 2-trifluoromethylphenyl isocyanate, which is reacted with dimethylsulfoxide to obtain N-(2-trifluoromethylphenyl)-S,S-dimethylsulfilimine, rearranged to a 2-(methylthiomethyl)-6-trifluoromethylaniline, and desulfurized to 2-methyl-6-trifluoromethyl aniline.

23. The process of claim 18 in which the nitrobenzene is converted to an aniline compound and then reacted with phosgene to form a phenyl isocyanate.

24. The process of claim 18 in which 2-methyl-6-trifluoromethyl aniline is prepared by reacting 1-nitro-2-trifluromethylbenzene with carbon monoxide at elevated pressure over a noble metal catalyst to obtain 2-trifluoromethylphenyl isocyanate, such isocyanate is reacted with dimethyl sulfoxide in the presence of strong acid to produce 2-trifluoromethylphenyl-S,S-dimethylsulfilimine; the sulfilimine is rearranged in the presence of a rearrangement catalyst to 2-methylthiomethyl-6-trifluoromethylaniline and desulfurized under reductive conditions to obtain 2-methyl-6-trifluoromethylaniline.

* * * * *